United States Patent [19]

Jessel, Jr.

[11] Patent Number: Plant 7,514

[45] Date of Patent: May 7, 1991

[54] CARNATION PLANT NAMED CFPC TWILIGHT

[75] Inventor: Walter H. Jessel, Jr., Salinas, Calif.

[73] Assignee: California Florida Plant Company L.P., Salinas, Calif.

[21] Appl. No.: 478,191

[22] Filed: Feb. 9, 1990

[51] Int. Cl.[5] ..... A01H 5/00

[52] U.S. Cl. ..... Plt./70

[58] Field of Search ..... Plt. 70–73

*Primary Examiner*—James R. Feyrer

*Attorney, Agent, or Firm*—James R. Cypher

[57] ABSTRACT

The present invention relates to a new and distinct cultivar of Carnation plant named CFPC Twilight, a cross from breeding patented, (U.S. Plant Pat. No. 5,580) commercially available, seed parent Carnation plant named Pamela and unnamed and unpatented pollen parent identified as No. 00715, distinguished from its parents, as well as any other variety known to me, by its bright purple color, abundant and stable production, fast growing response which does not slow down during cool periods, and small flower size with smooth petals yielding a "petite" appearance, a characteristic currently in-demand by the commercial flower industry.

1 Drawing Sheet

BACKGROUND OF THE INVENTION

The present invention relates to a new and distinct cultivar of Carnation plant named CFPC Twilight which was originated by me from a cross made in a controlled breeding program at commercial nurseries at Fremont and Salinas, Calif. The female, or seed parent was the unpatented, commercially available Carnation plant named Pamela. The male, or pollen parent, was unnamed and patented (U.S. Plant Pat. No. 5,580) Carnation plant identified as No. 00715.

The primary objectives of this breeding were to produce a carnation cultivar of bright purple color; abundant production with a fast growing response which would not slow down during cool periods; and a smooth petal-edge, a characteristic which has become increasingly popular and in-demand by the commercial carnation flower market.

These objectives were fully achieved, along with other desirable improvements, as evidenced by the following unique combination of principal characteristics which are outstanding in my new cultivar, CFPC Twilight, and which distinguish it from its parents, as well as from all other carnations of which I am aware. The closest commercial cultivar in color to the new cultivar is the commercially available, unpatented Carnation plant named Sharon.

The distinguishing characteristics which are outstanding in the new cultivar are as follows:

1. small, spray-type flowers which open fully without bursting the clayx and causing "splits";
2. a distinctive bright purple flower color;
3. a very vigorous and free-breaking plant habit with strong, straight sprays;
4. pinched plants are shorter than pinched plants of Sharon;
5. The flower diameter averages ¾" smaller than Sharon and the crown is flatter;
6. flowering time is six to seven weeks earlier than Sharon;
7. color is lighter and brighter than Sharon;
8. petals are smooth yielding a "petite" appearance; and 9. vase-life is the same as Sharon's under equal conditions.

Asexual reproduction and flowerings of the new cultivar where performed by Applicant using side shoot cuttings rooted in peat and "Perlite" under mist, in commercial greenhouses located at Fremont and Salinas, Calif. The new cultivar was found to retain its distinctive characteristics as listed herein through successive propagations.

BRIEF DESCRIPTION OF THE DRAWING

The accompanying color photograph illustrates typical specimens of the new carnation in different stages of development (tight buds, partially opened buds and flowers in full bloom) and shows the bright, purple color and vigorous, free-breaking growth habit and strong, straight stems of CFPC Twilight. The color photograph depicts the color as nearly true as it is reasonably possible to do in a color illustration of this character.

DETAILED DESCRIPTION OF THE DRAWING

The following is a detailed description of the new carnation plant of the present invention based on observations of plants grown inside commercial greenhouses at Fremont and Salinas, Calif.; the height of plant, and flower and foliage size established as an average using standard commercial cultural practices. The data provided accurately characterizes the new cultivar in question. The color terminology used in the following is in accordance with The Royal Horticultural Society Color Chart. Color designation and other values stated may deviate slightly from the stated values from flowering to flowering, but the deviations will be within the range expected from varying environmental, seasonal and cultural conditions.

PLANT

Name: CFPC Twilight.

Classification:

*Botanical.—Dianthus caryophyllus.*

*Commercial.*—Carnation, greenhouse type, suitable for cut flower production as a spray.

Origin:

*Female parent.*—Patented (U.S. Plant Pat. No. 5,580) commercially available Carnation plant named Pamela.

*Male parent.*—Unnamed and unpatented Carnation plant identified as No. 00715.

The following table compares the new cultivar with its closest commercial variety of which I am aware.

TABLE OF COMPARISON

| New Cultivar CFPC TWILIGHT | SHARON |
|---|---|
| PLANT: | |
| Height thirty-two inches (32") | forty inches (40") |
| Form: smooth, round flattened | serrated, round |
| crown | high crown |
| Growing Habit: stiff, semi-upright | same |
| Blooming Habit: spray | same |
| Blooming Season: year-round | same |
| Rooting Time/Habit: 18 to 20 days | same |
| Stem: | |
| Color: green | same |
| Breaking action: excellent | average |
| Mutation Prone No | same |
| Temperature Tolerance: excellent | good to fair |
| FOLIAGE: | |
| Color - Upper side 139B | same |
| Lower side 138B | same |
| Size: 1¾" to 4" long | 2" to 4¾" long |
| ¼" to ⅜" wide | ⅜" to ⅝" wide |
| Quantity: numerous | same |
| Shape: lanceolate pointed elongated | pointed elongated |
| Texture: smooth | same |

-continued

TABLE OF COMPARISON

| New Cultivar CFPC TWILIGHT | SHARON |
|---|---|
| Ribs: indented mid-rib | same |
| Arrangement: bi-laterial at nodes | same |
| BLOOM: | |
| Form: spray | same |
| Shape: round, smooth petite | larger, more course |
| appearance | appearance |
| Inflorescence: 8 to 10 per stem | 6 to 9 per stem |
| Flower: diameter average: 1¾" to 2¼" | 2" to 3½" |
| depth average ¾" | 1½" |
| Borne: on elongated peduncles | same |
| Color: general tonality: bright purple | dark purple |
| Upper side: red-purple 72A-71B | red-purple 71A to 72A |
| Lower side: 71C | 72A |
| Center: 72A-71B | 71A-72A |
| Outer petals: 72A-71B | 71A-72A |
| Permanence yes | same |
| Keeping habit: 8 to 10 days | same |
| Fragrance: slight | same |
| PETALAGE: | |
| Number: 19 to 22 | 21 to 23 |
| Outer petals, length ¾"-⅞" | 1¼" to 1½" |
| width ⅝" | ¾" |
| Central petals, length ½" | ¾" |
| width ⅝" | ¾" |
| Texture: smooth | same |
| Appearance: smooth | serrated |
| Form: fan-shaped | same |
| REPRODUCTION ORGANS: | |
| Stamen: arrangement: whorled | same |
| anthers: color: purple | dark red-purple |
| Pistil: number: 2 | same |
| stigma: 2 | same |
| Pollen: color: purple-white | same |
| abundant: yes | same |
| Fertility: fair | good |

I claim:

1. A new and distinctive cultivar of Carnation plant, named CFPC Twilight substantially as herein shown and described.

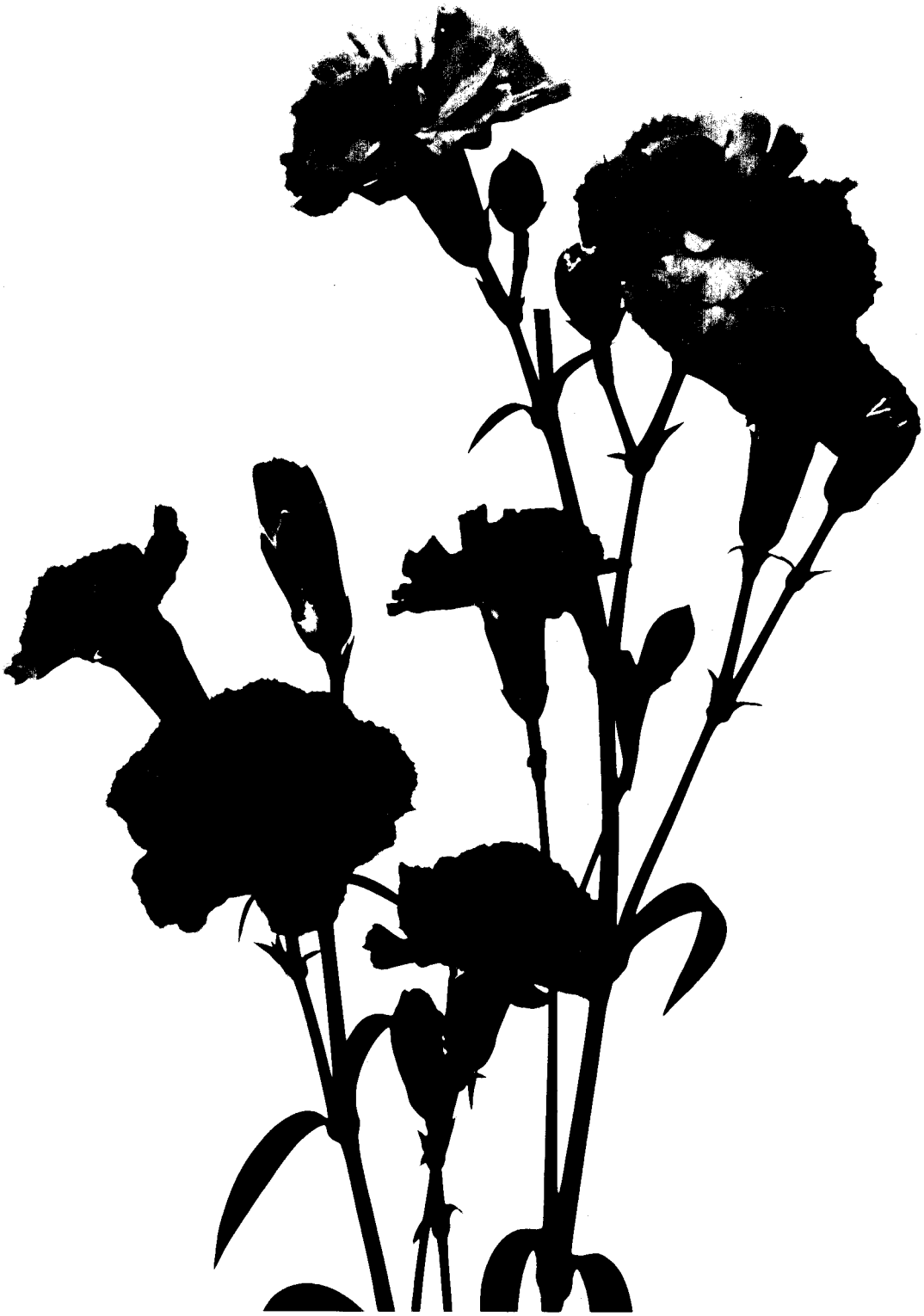

* * * * *